(12) United States Patent
Maruta et al.

(10) Patent No.: US 8,216,818 B2
(45) Date of Patent: Jul. 10, 2012

(54) KETOSE 3-EPIMERASE, ITS PREPARATION AND USES

(75) Inventors: Kazuhiko Maruta, Okayama (JP); Kozo Yamamoto, Okayama (JP); Tomoyuki Nishimoto, Okayama (JP); Hiroto Chaen, Okayama (JP); Tetsuya Nakada, Okayama (JP)

(73) Assignee: Kabushiki Kaisha Hayashibara Seibutsu Kagaku Kenkyujo, Okayama (JP)

( * ) Notice: Subject to any disclaimer, the term of this patent is extended or adjusted under 35 U.S.C. 154(b) by 0 days.

(21) Appl. No.: 13/187,718

(22) Filed: Jul. 21, 2011

(65) Prior Publication Data

US 2011/0275138 A1  Nov. 10, 2011

Related U.S. Application Data

(62) Division of application No. 12/093,902, filed as application No. PCT/JP2006/322105 on Nov. 6, 2006, now Pat. No. 8,008,058.

(30) Foreign Application Priority Data

Nov. 15, 2005 (JP) .................. 2005-329683
Jul. 14, 2006 (JP) .................. 2006-194037

(51) Int. Cl.
*C07H 21/00* (2006.01)
*C12N 1/21* (2006.01)
*C12N 5/10* (2006.01)
*C12N 15/00* (2006.01)
*C12P 21/00* (2006.01)
*C12N 9/90* (2006.01)

(52) U.S. Cl. ............ 435/233; 435/252.3; 435/325; 435/320.1; 435/69.1; 536/23.2

(58) Field of Classification Search .......... 435/233, 435/69.1, 320.1, 252.3, 325; 530/350; 536/23.2
See application file for complete search history.

(56) References Cited

FOREIGN PATENT DOCUMENTS

| JP | 2001011090 | 1/2001 |
|---|---|---|
| JP | 2005213227 | 8/2005 |

OTHER PUBLICATIONS

GenBank accession No. AM236086 (Sep. 20, 2006).*
Database, UniProt,"SubName:Full=Putative-epimerase," retrieved from EBI accession No. UNIPROT: Q1M4R4, 2006.
Ishida et al.,"Cloning and characterization of the D-tagatose 3-epimerase gene from *Pseudomonas cichorii* ST-24," Journal of fermentation and bioengineering, 1997, pp. 529-534, vol. 83, No. 6.
Ken izumor et al., A New Enzyme, D-Ketohexose 3-Epimerase, from *Pseudomonas* sp. ST-24, Biosci, Biotech, Biochem, (1993), vol. 57(6), pp. 1037-1039.
Keiji Tsuzaki et al., *Rhizobium legminosarum* ATTC 14480 Yurai D-Psicose 3-Epimerase no Seishitsu to Idenshi Cloning, The Society for Biotechnology, Japan Taikai Koen Yoshishu, (2006), vol. 58, p. 95.
Turlough M. Finan et al., The complete sequence of the 1,683-kb pSymB megaplasmid from the N2-ficing endosymbiont *Sinorhizobioum meiloti*, PNAS, (2001), vol. 98 (17), pp. 9889-9894.
Hye-Jung Kim et al., Characterization of an *Agrobacterium tumefaciens* D-Psicose 3-Epimerase that Converts D-Fructose to D-Psicose, Applied and Environmental Microbiology, (2006), vol. 72(2), pp. 981-985.
A. M. Buendia et al., The *Rhizobium meliloti* exoZ/exoB fragment of megaplasmid 2:ExoB functions as a UDP-glucose 4-epimerase and ExoZ shows homology to NodX of *Rhizobiurn leguminosarum* biovar viciae strain TOM, Molecular Microbiology, (1991), vol. 5 (6), pp. 1519-1530.
Branden et al., Introduction to Protein Structure, Garland Publishing Inc., New York, p. 247, 1991.
Seffernick et al., J. Bacteriol. 183(8):2405-2410, 2001.
Witkowski et al., Biochemistry 38:11643-11650, 1999.
Itoh et al., Biosci. Biotech. Biochem. 58(12):2168-2171, 1994.
Finan et al., GenBank accession No. CAC48870, 2001.

* cited by examiner

*Primary Examiner* — Delia Ramirez
(74) *Attorney, Agent, or Firm* — Browdy and Neimark, PLLC

(57) ABSTRACT

An object of the present invention is to provide a novel ketose 3-epimerase, a process for producing the same, a DNA encoding the enzyme, a recombinant DNA and transformant comprising the DNA, and a process for producing a ketose by using the enzyme. The present invention solves the above objects by providing a ketose 3-epimerase which is obtainable from a microorganism of the genus *Rhizobium*, a process for producing the same, a DNA encoding the enzyme, a recombinant DNA and transformant comprising the DNA, and a process for converting D- or L-ketohexose into corresponding D- or L-ketohexose by epimerizing the hydroxyl group at the C-3 position of the D- or L-ketohexose; and D- or L-ketopentose into corresponding D- or L-ketopentose by epimerizing the hydroxyl group at the C-3 position of the D- or L-ketopentose; by using the enzyme.

7 Claims, 3 Drawing Sheets

SEQUENCE LISTING

<160> NUMBER OF SEQ ID NOS: 13

<210> SEQ ID NO 1
<211> LENGTH: 10
<212> TYPE: PRT
<213> ORGANISM: Rhizobium leguminosarum

<400> SEQUENCE: 1

Met Glu Gly Phe Gly Val His Thr Ser Met
1               5                   10

<210> SEQ ID NO 2
<211> LENGTH: 282
<212> TYPE: PRT
<213> ORGANISM: Rhizobium leguminosarum

<400> SEQUENCE: 2

Met Glu Gly Phe Gly Val His Thr Ser Met Trp Thr Met Asn Trp Asp
1               5                   10                  15

Arg Ala Gly Ala Glu Lys Ala Ile Ala Gly Ala Val His Tyr Lys Met
            20                  25                  30

Asp Phe Ile Glu Ile Ala Leu Leu Asn Ala Pro Ala Val Asp Ala Lys
        35                  40                  45

His Thr Arg Ala Leu Leu Glu Lys Asn Lys Leu Arg Ala Val Cys Ser
    50                  55                  60

Leu Gly Leu Pro Glu His Ala Trp Ala Ser Val Arg Pro Asp Ala Ala
65                  70                  75                  80

Ile Glu His Leu Lys Val Ala Ile Glu Lys Thr Ala Glu Met Asn Ala
                85                  90                  95

Glu Ala Leu Ser Gly Val Ile Phe Gly Ile Gly Glu Arg Thr Gly
            100                 105                 110

Val Pro Pro Thr Gln Gly Glu Tyr Asp Asn Ile Ala Lys Val Leu Asp
        115                 120                 125

Val Ala Ala Lys His Ala Arg Lys His Gly Ile Gln Leu Gly Val Glu
    130                 135                 140

Ala Val Asn Arg Tyr Glu Asn His Leu Ile Asn Ser Ala Gln Gln Ala
145                 150                 155                 160

Val Asp Met Val Glu Arg Val Gly Ala Asp Asn Ile Phe Val His Leu
                165                 170                 175

Asp Thr Tyr His Met Asn Ile Glu Glu Lys Gly Ala Ala Asn Gly Ile
            180                 185                 190

Leu Ile Ala Arg Asp His Leu Lys Tyr Ile His Leu Ser Glu Ser Asp
        195                 200                 205

Arg Gly Thr Pro Gly Tyr Gly Asn Ile Pro Trp Asp Ala Ile Tyr Ala
    210                 215                 220

Ala Leu Ala Ala Ile Gly Phe Lys Gly Leu Ala Met Glu Ser Phe
225                 230                 235                 240

Ile Asn Met Pro Pro Glu Val Ala Tyr Gly Leu Ala Val Trp Arg Pro
                245                 250                 255

Val Ala Arg Asp Met Glu Glu Val Met Asp Lys Gly Leu Pro Phe Leu
            260                 265                 270

Arg Asn Lys Ala Glu Gln Tyr Gly Leu Ile
        275                 280

<210> SEQ ID NO 3
<211> LENGTH: 846

```
<212> TYPE: DNA
<213> ORGANISM: Rhizobium leguminosarum
<220> FEATURE:
<221> NAME/KEY: CDS
<222> LOCATION: (1)..(846)

<400> SEQUENCE: 3 atg gaa ggt ttc ggc gtt cac acc agc atg tgg acc atg aac tgg gat        48
Met Glu Gly Phe Gly Val His Thr Ser Met Trp Thr Met Asn Trp Asp
1               5                   10                  15 cgc gca ggt gcc gaa aag gcg att gcc gga gcc gtg cac tac aag atg        96
Arg Ala Gly Ala Glu Lys Ala Ile Ala Gly Ala Val His Tyr Lys Met
            20                  25                  30 gat ttc atc gag atc gcg ctg ctg aac gcg cct gcc gtc gat gcc aaa       144
Asp Phe Ile Glu Ile Ala Leu Leu Asn Ala Pro Ala Val Asp Ala Lys
        35                  40                  45 cac acc cgc gcc ctg ctt gaa aag aat aag ctg cgc gcc gtc tgc tcg       192
His Thr Arg Ala Leu Leu Glu Lys Asn Lys Leu Arg Ala Val Cys Ser
    50                  55                  60 ctc ggc ctg ccg gaa cat gcc tgg gcc tcg gtc cgc ccg gat gcc gca       240
Leu Gly Leu Pro Glu His Ala Trp Ala Ser Val Arg Pro Asp Ala Ala
65                  70                  75                  80 atc gag cac ctg aag gtt gcg atc gaa aag act gca gaa atg aac gcc       288
Ile Glu His Leu Lys Val Ala Ile Glu Lys Thr Ala Glu Met Asn Ala
                85                  90                  95 gag gcc ctg tcc ggc gtc atc ttc ggc ggc atc ggc gag cgc acc ggc       336
Glu Ala Leu Ser Gly Val Ile Phe Gly Gly Ile Gly Glu Arg Thr Gly
            100                 105                 110 gtg cca ccg acg cag ggc gaa tac gac aac atc gcc aag gtc ctc gac       384
Val Pro Pro Thr Gln Gly Glu Tyr Asp Asn Ile Ala Lys Val Leu Asp
        115                 120                 125 gta gcg gca aag cat gct agg aag cac ggc atc cag ctc ggc gtc gag       432
Val Ala Ala Lys His Ala Arg Lys His Gly Ile Gln Leu Gly Val Glu
    130                 135                 140 gcc gtg aac cgc tat gag aac cac ctg atc aac tcg gcg cag cag gcc       480
Ala Val Asn Arg Tyr Glu Asn His Leu Ile Asn Ser Ala Gln Gln Ala
145                 150                 155                 160 gtc gac atg gtg gag cgc gtc ggc gcg gat aac atc ttc gtt cac ctc       528
Val Asp Met Val Glu Arg Val Gly Ala Asp Asn Ile Phe Val His Leu
                165                 170                 175 gac acc tac cac atg aat atc gag gaa aag ggt gcg gca aat ggc atc       576
Asp Thr Tyr His Met Asn Ile Glu Glu Lys Gly Ala Ala Asn Gly Ile
            180                 185                 190 ctg atc gcc cgc gat cac ctg aag tac atc cat ctt tcg gaa agc gac       624
Leu Ile Ala Arg Asp His Leu Lys Tyr Ile His Leu Ser Glu Ser Asp
        195                 200                 205 cgc ggc aca ccg ggc tac ggc aac atc ccg tgg gat gcg atc tat gcc       672
Arg Gly Thr Pro Gly Tyr Gly Asn Ile Pro Trp Asp Ala Ile Tyr Ala
    210                 215                 220 gcg ctc gcc gca atc ggc ttc aag ggc ggg ctt gcg atg gaa agc ttc       720
Ala Leu Ala Ala Ile Gly Phe Lys Gly Gly Leu Ala Met Glu Ser Phe
225                 230                 235                 240 atc aac atg ccg cct gag gtc gcc tat ggc ctg gcc gtc tgg cgc ccc       768
Ile Asn Met Pro Pro Glu Val Ala Tyr Gly Leu Ala Val Trp Arg Pro
                245                 250                 255 gtt gca cgc gat atg gaa gag gtc atg gac aag ggc ctg ccg ttc ctg       816
Val Ala Arg Asp Met Glu Glu Val Met Asp Lys Gly Leu Pro Phe Leu
            260                 265                 270 cgc aat aag gcg gaa caa tac ggt ctc atc                               846
Arg Asn Lys Ala Glu Gln Tyr Gly Leu Ile
        275                 280
```

<210> SEQ ID NO 4
<211> LENGTH: 282
<212> TYPE: PRT
<213> ORGANISM: Sinorhizobium meliloti

<400> SEQUENCE: 4

Met Gln Gly Phe Gly Val His Thr Ser Met Trp Thr Met Asn Trp Asp
1               5                   10                  15

Arg Pro Gly Ala Glu Arg Ala Val Ala Ala Val Lys Tyr Lys Val
            20                  25                  30

Asp Phe Ile Glu Ile Pro Met Leu Asn Pro Ala Val Asp Thr Glu
        35                  40                  45

His Thr Arg Gly Leu Leu Glu Lys Ser Arg Leu Arg Ala Val Cys Ser
    50                  55                  60

Leu Gly Leu Pro Glu Arg Ala Trp Ala Ser Val Arg Pro Glu Ala Ala
65                  70                  75                  80

Ile Asp His Leu Lys Ile Ala Ile Asp Lys Thr Ala Asp Leu Gly Gly
                85                  90                  95

Glu Ala Leu Ser Gly Val Ile Tyr Gly Gly Ile Gly Glu Arg Thr Gly
            100                 105                 110

Val Pro Pro Thr Val Glu Glu Tyr Asp Asn Ile Ala Arg Val Leu Gln
        115                 120                 125

Ala Ala Ala Lys His Ala Lys Ser Arg Gly Ile Glu Leu Gly Val Glu
    130                 135                 140

Ala Val Asn Arg Tyr Glu Asn His Leu Ile Asn Thr Gly Trp Gln Ala
145                 150                 155                 160

Val Lys Met Ile Glu Arg Val Gly Ala Asp Asn Val Phe Val His Leu
                165                 170                 175

Asp Thr Tyr His Met Asn Ile Glu Glu Lys Gly Val Gly Lys Gly Ile
            180                 185                 190

Leu Asp Ala Arg Glu His Leu Lys Tyr Ile His Leu Ser Glu Ser Asp
        195                 200                 205

Arg Gly Thr Pro Gly Tyr Gly Thr Cys Gly Trp Asp Glu Ile Phe Ser
    210                 215                 220

Thr Leu Ala Ala Ile Gly Phe Lys Gly Gly Leu Ala Met Glu Ser Phe
225                 230                 235                 240

Ile Asn Met Pro Pro Glu Val Ala Tyr Gly Leu Ala Val Trp Arg Pro
                245                 250                 255

Val Ala Lys Asp Glu Glu Glu Val Met Gly Asn Gly Leu Pro Phe Leu
            260                 265                 270

Arg Asn Lys Ala Thr Gln Tyr Gly Leu Ile
        275                 280

<210> SEQ ID NO 5
<211> LENGTH: 846
<212> TYPE: DNA
<213> ORGANISM: Sinorhizobium meliloti
<220> FEATURE:
<221> NAME/KEY: CDS
<222> LOCATION: (1)..(846)

<400> SEQUENCE: 5 atg cag ggt ttt ggc gtt cat acg agc atg tgg aca atg aat tgg gac     48
Met Gln Gly Phe Gly Val His Thr Ser Met Trp Thr Met Asn Trp Asp
1               5                   10                  15 cgt ccc ggc gcc gaa cgg gcg gta gcc gca gcg gtc aaa tac aag gtc     96
Arg Pro Gly Ala Glu Arg Ala Val Ala Ala Ala Val Lys Tyr Lys Val
            20                  25                  30

```
gat ttc atc gag atc ccg atg ctc aat ccg cct gcc gtc gac acg gag    144
Asp Phe Ile Glu Ile Pro Met Leu Asn Pro Pro Ala Val Asp Thr Glu
         35                  40                  45 cac acc cgt ggc ctc ctc gag aaa agc cgt ctg cgc gcg gtc tgc tcg    192
His Thr Arg Gly Leu Leu Glu Lys Ser Arg Leu Arg Ala Val Cys Ser
 50                  55                  60 ctc ggc ctg ccg gag cgg gcc tgg gcc tcg gtt cgg ccc gag gcg gcg    240
Leu Gly Leu Pro Glu Arg Ala Trp Ala Ser Val Arg Pro Glu Ala Ala
65                  70                  75                  80 atc gac cat ctg aag atc gcg atc gac aag act gcc gat ctc ggc ggc    288
Ile Asp His Leu Lys Ile Ala Ile Asp Lys Thr Ala Asp Leu Gly Gly
                 85                  90                  95 gag gcg ctg tcg ggc gtc atc tat ggc ggc atc ggc gag cgc acc ggc    336
Glu Ala Leu Ser Gly Val Ile Tyr Gly Gly Ile Gly Glu Arg Thr Gly
            100                 105                 110 gtg ccg ccg acc gtc gag gag tat gac aat atc gcc cgc gtg ctg cag    384
Val Pro Pro Thr Val Glu Glu Tyr Asp Asn Ile Ala Arg Val Leu Gln
        115                 120                 125 gcc gcg gcc aag cac gcc aag tcg cgc ggc atc gag ctt ggc gtc gaa    432
Ala Ala Ala Lys His Ala Lys Ser Arg Gly Ile Glu Leu Gly Val Glu
    130                 135                 140 gcc gtc aac cgc tac gag aac cac ctg atc aat acc ggc tgg cag gcg    480
Ala Val Asn Arg Tyr Glu Asn His Leu Ile Asn Thr Gly Trp Gln Ala
145                 150                 155                 160 gtc aag atg atc gag cgg gtc gga gcc gac aac gtc ttc gtg cac ctc    528
Val Lys Met Ile Glu Arg Val Gly Ala Asp Asn Val Phe Val His Leu
                165                 170                 175 gat acc tat cac atg aac atc gag gaa aag ggc gtc ggc aaa ggt atc    576
Asp Thr Tyr His Met Asn Ile Glu Glu Lys Gly Val Gly Lys Gly Ile
            180                 185                 190 ctc gat gcc cgc gag cac ctg aaa tac atc cat ctt tcc gaa agc gac    624
Leu Asp Ala Arg Glu His Leu Lys Tyr Ile His Leu Ser Glu Ser Asp
        195                 200                 205 cgc ggc acg ccg ggc tac ggc acc tgc ggc tgg gac gag att ttc tcg    672
Arg Gly Thr Pro Gly Tyr Gly Thr Cys Gly Trp Asp Glu Ile Phe Ser
    210                 215                 220 acg ctt gcg gcg atc ggc ttc aag ggc ggc ctc gcc atg gaa agc ttc    720
Thr Leu Ala Ala Ile Gly Phe Lys Gly Gly Leu Ala Met Glu Ser Phe
225                 230                 235                 240 atc aac atg ccg ccg gaa gtg gcc tat ggc ctc gcc gtc tgg cgc ccg    768
Ile Asn Met Pro Pro Glu Val Ala Tyr Gly Leu Ala Val Trp Arg Pro
                245                 250                 255 gtc gca aag gac gag gaa gag gtg atg ggc aac ggc ctg ccg ttc ctg    816
Val Ala Lys Asp Glu Glu Glu Val Met Gly Asn Gly Leu Pro Phe Leu
            260                 265                 270 cgc aac aag gcc acg cag tac ggc ctg atc                            846
Arg Asn Lys Ala Thr Gln Tyr Gly Leu Ile
        275                 280

<210> SEQ ID NO 6
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (9)..(9)
<223> OTHER INFORMATION: n is a, c, g, or t

<400> SEQUENCE: 6
atgtggacna tgaaytggga                                               20
```

<210> SEQ ID NO 7
<211> LENGTH: 20
<212> TYPE: DNA
<213> ORGANISM: Artificial Sequence
<220> FEATURE:
<223> OTHER INFORMATION: Synthetic

<400> SEQUENCE: 7
tcytcdatrt tcatrtgrta                                          20

<210> SEQ ID NO 8
<211> LENGTH: 26
<212> TYPE: DNA
<213> ORGANISM: Artificial Sequence
<220> FEATURE:
<223> OTHER INFORMATION: Synthetic

<400> SEQUENCE: 8
tcaactcggc gcagcaggcc gtcgac                                   26

<210> SEQ ID NO 9
<211> LENGTH: 26
<212> TYPE: DNA
<213> ORGANISM: Artificial Sequence
<220> FEATURE:
<223> OTHER INFORMATION: Synthetic

<400> SEQUENCE: 9
tgacgccgga cagggcctcg gcgttc                                   26

<210> SEQ ID NO 10
<211> LENGTH: 26
<212> TYPE: DNA
<213> ORGANISM: Artificial Sequence
<220> FEATURE:
<223> OTHER INFORMATION: Synthetic

<400> SEQUENCE: 10
tggtggagcg cgtcggcgcg gataac                                   26

<210> SEQ ID NO 11
<211> LENGTH: 26
<212> TYPE: DNA
<213> ORGANISM: Artificial Sequence
<220> FEATURE:
<223> OTHER INFORMATION: Synthetic

<400> SEQUENCE: 11
gcagtctttt cgatcgcaac cttcag                                   26

<210> SEQ ID NO 12
<211> LENGTH: 34
<212> TYPE: DNA
<213> ORGANISM: Artificial Sequence
<220> FEATURE:
<223> OTHER INFORMATION: Synthetic

<400> SEQUENCE: 12
aaaaacatat ggaaggtttc ggcgttcaca ccag                          34

<210> SEQ ID NO 13
<211> LENGTH: 35
<212> TYPE: DNA
<213> ORGANISM: Artificial Sequence
<220> FEATURE:
<223> OTHER INFORMATION: Synthetic

```
<400> SEQUENCE: 13
aaaaagaatt ctcagatgag accgtattgt tccgc                                      35
```

KETOSE 3-EPIMERASE, ITS PREPARATION AND USES

TECHNICAL FIELD

The present invention relates to a ketose 3-epimerase, its preparation and uses, particularly, to a ketose 3-epimerase, which is obtainable from a microorganism of the genus *Rhizobium* and has the following substrate specificity; a DNA encoding the enzyme; a recombinant DNA and a transformant comprising the DNA; and a process for producing a ketose by using the enzyme:

(1) Epimerizing a hydroxyl group at the C-3 position of D- or L-ketohexose to form corresponding D- or L-ketohexose and that of D- or L-ketopentose to form corresponding D- or L-ketopentose; and (2) Most specific to D-fructose and D-psicose among D- or L-ketohexose and D- or L-ketopentose.

BACKGROUND ART

Japanese Patent Kokai No. 11,090/2001 disclosed that D-psicose can be advantageously used as a low-calorie sweetener for producing low-calorie foods and beverages. In addition, Japanese Patent Kokai No. 213,227/2005 disclosed that D-psicose can be advantageously used for health foods, foods and beverages for diabetic patients, and foods and beverages for sliming.

Ken Izumori et al., Biosci. Biotech. Biochem., 57, 1037-1039 (1993) disclosed a D-ketohexose 3-epimerase from *Pseudomonas cichorii* ST-24 and that D-psicose can be produced from D-fructose by using the enzyme. However, the enzyme is sometimes referred to as "D-tagatose 3-epimerase" and is known to be an enzyme most specific to D-tagatose and having a relatively low activity on D- fructose. Further, *Pseudomonas cichorii* is not preferable to use for industrial production because the bacterium is a phytopathogenic microorganism and its ability to produce the D-ketohexose 3-epimerase is very low. Under the circumstances, a microorganism with a high ability to produce a ketose 3-epimerase, except for the genus *Pseudomonas*, and a ketose 3-epimerase with a high specificity D- fructose, being preferable for the production of D-psicose, are desired.

DISCLOSURE OF INVEVTION

An object of the present invention is to provide a novel ketose 3-epimerase a process for producing the same, a DNA encoding the enzyme, a recombinant DNA and transformant comprising the DNA, and a process for producing ketoses by using the enzyme.

The present inventors have extensively screened microorganisms, capable of producing a ketose 3-epimerase, except for the genus *Pseudomonas*. As a result, the present inventors isolated a novel microorganism of the genus *Rhizobium* producing a novel ketose 3 -epmerase. The present inventors found that the novel ketose 3-epimerase derived from the microorganism exhibits a wide substrate specificity acting on D- or L-ketopentose as well as D- or L-ketohexose and catalyzing the epimerization to form corresponding D- or L-ketose. The present inventors also found that the enzyme is, unexpectedly, most specific to D-fructose and D-psicose and preferable to use for the production of D-psicose from D-fructose. The present inventors accomplished the present invention by establishing the novel ketose 3-epimerase obtainable from a microorganism of the genus *Rhizobium*; a process for producing the enzyme; a DNA encoding the enzyme; a recombinant DNA comprising the DNA; a transformant; a method for converting ketoses by using the enzyme; and a process for producing ketoses by using the enzyme.

The present invention solves the above objects by providing a ketose 3-epimerase which is obtainable from a microorganism of the genus *Rhizobium*, a process for producing the same, a DNA encoding the enzyme, a recombinant DNA and a transformant comprising the DNA, and a process for converting D- or L-ketohexose into corresponding D- or L-ketohexose by epimerizing the hydroxyl group at the C-3 position of the D- or L-ketohexose; and D- or L-ketopentose into corresponding D- or L-ketopentose by epimerizing the hydroxyl group at the C-3 position of the D- or L-ketopentose; by using the enzyme.

The microorganism of the genus *Rhizobium* has a high ability to produce the novel ketose 3-epimerase and no phytopathogenicity different to *Pseudomonas cichorii*. Further, since the ketose 3-epimerase of the present invention, obtainable from the microorganism, can be used for converting D-psicose to D-fructose and vice versa, it is useful for the production of D-psicose from D-fructose.

In the figure, a section indicated with black bold line is a DNA encoding the ketose 3-epimerase originated from *Rhizobium leguminosarum* ATCC14480.

EXPLANATION OF SYMBOLS

In FIGS. 1 to 4,

•: in the absence of 1 mM $Mn^{2+}$ ion

○: in the presence of 1 mM $Mn^{2+}$ ion

Figure 1:
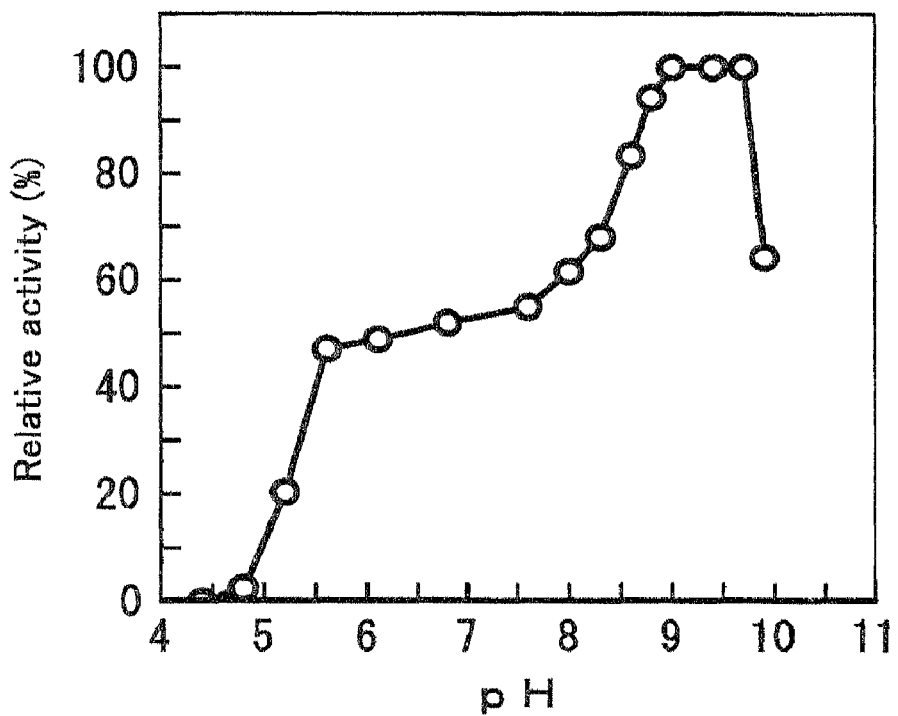
FIG. 1 shows the optimum pH of the ketose 3-epimerase of the present invention.
Figure 2:
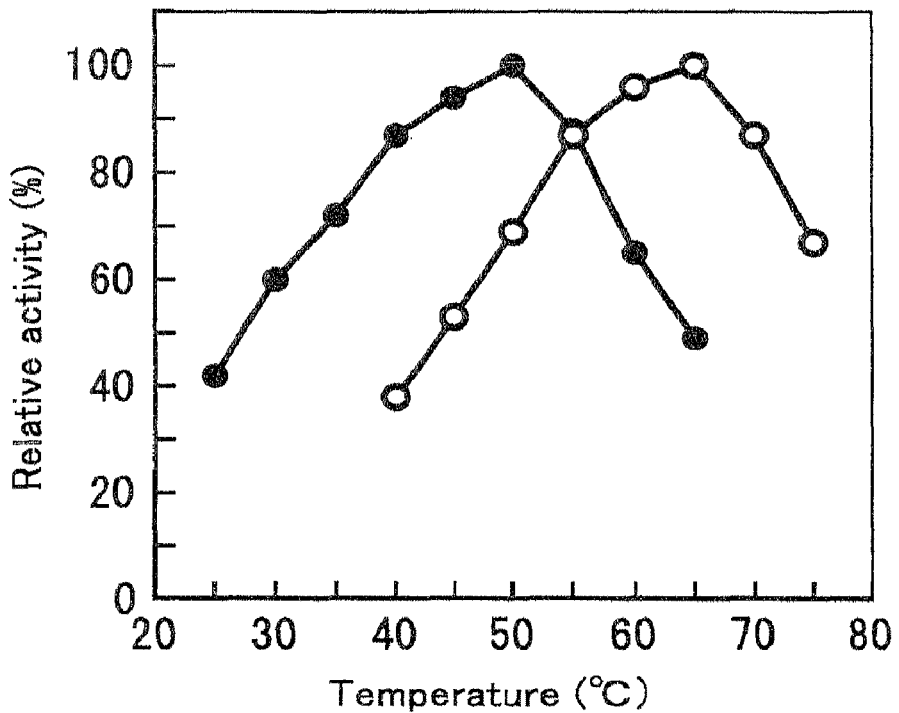
FIG. 2 shows the optimum temperature of the ketose 3-epimerase of the present invention.
Figure 3:
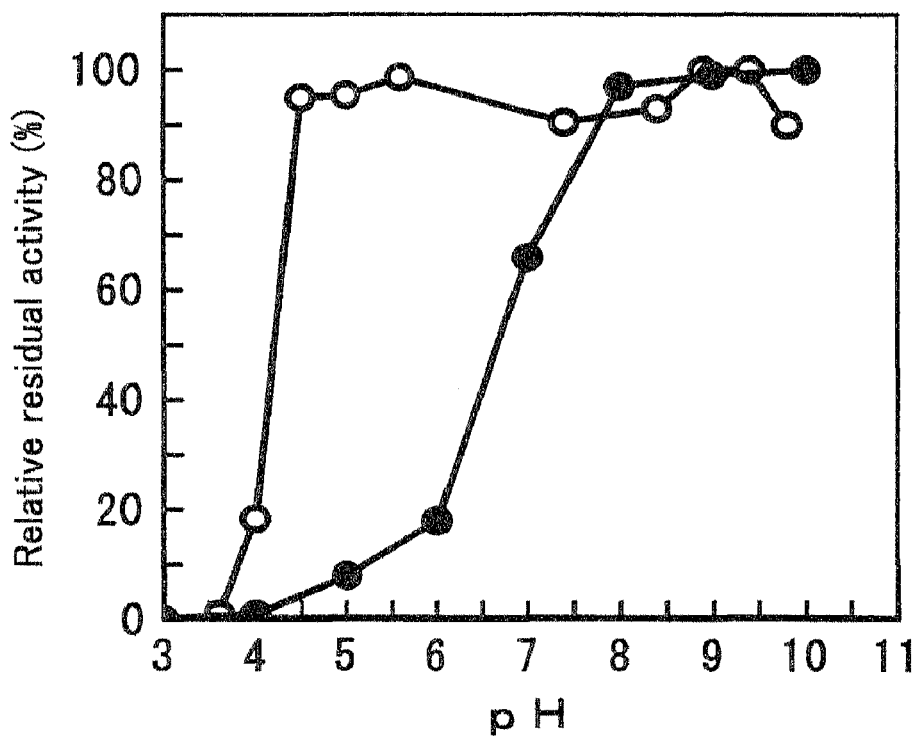
FIG. 3 shows the pH stability of the ketose 3-epimerase of the present invention.
Figure 4:
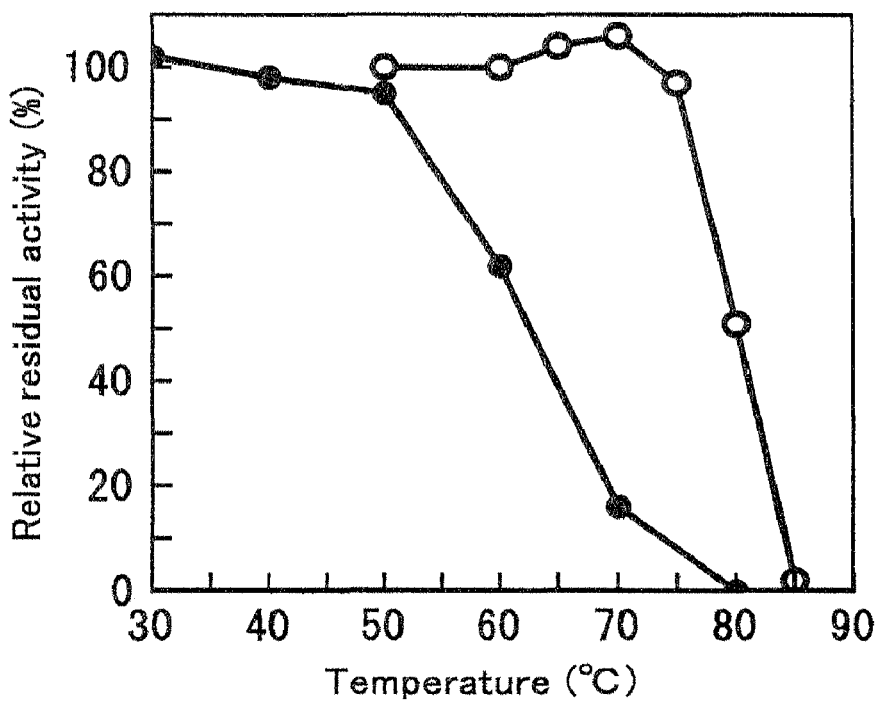
FIG. 4 shows the thermal stability of the ketose 3-epimerase of the present invention.
Figure 5:
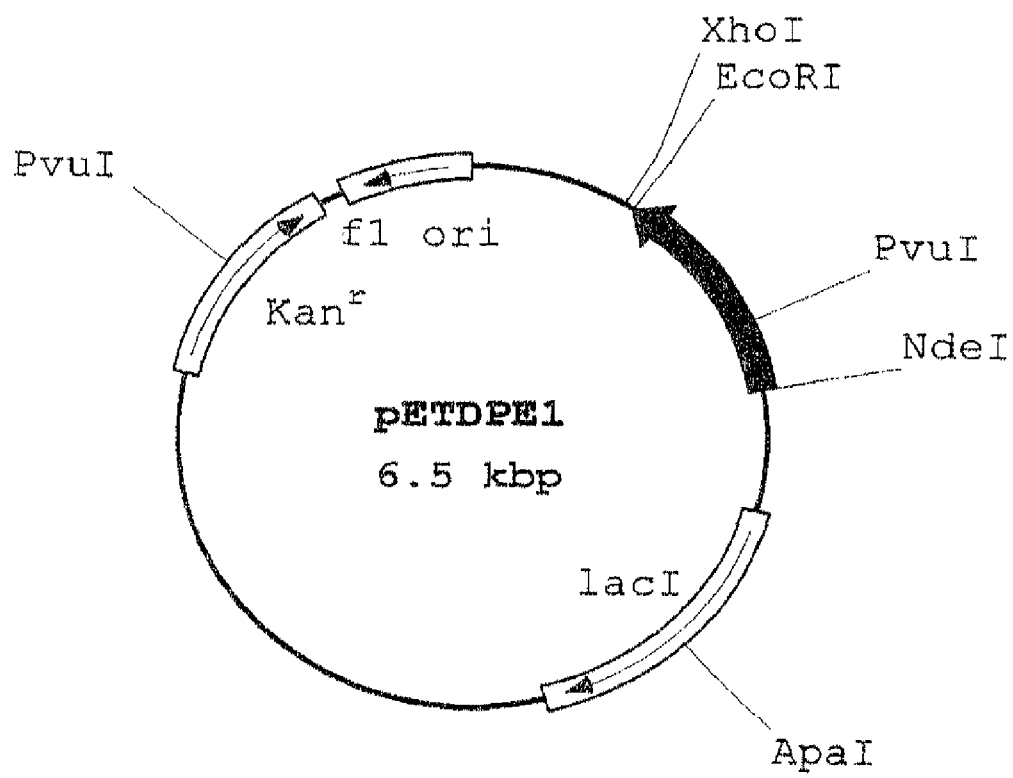
FIG. 5 shows a recombinant DNA, pETDPE1 for expressing the recombinant ketose 3-epimerase.

In FIG. 5, f1 (+) ori: Replication origin of f1 phage $Kan^r$: Kanamycin resistance gene lac I: lac repressor

BEST MODE FOR CARRYING OUT THE INVENTION

Ketohexoses as referred to as in the present invention mean hexoses having a ketose structure, specifically, fructose, psicose, tagatose, and sorbose; and D- or L-ketohexoses mean those D- or L-isomers. In a similar fashion, ketopentoses as referred to as in the present invention mean pentoses having a ketose structure, specifically, xylulose and ribulose; and D- or L-ketopentoses means those D- or L-isomers.

The ketose 3 -epimerase of the present invention has an activity of epimerizing the C-3 hydroxyl group of D- or L-ketohexose and forming corresponding D- or L-ketohexose; and catalyzes the conversion of D- or L-fructose into D- or L-psicose and vice versa, and D- or L-tagatose into D- or L-sorbose and vice versa. Also, the enzyme has an activity of epimerizing the C-3 hydroxyl group of D- or L-ketopentose and forming corresponding D- or L-ketopentose; and catalyzes the conversion of D- or L-xylulose into D- or L-ribulose and vice versa. The ketose 3-epimerase of the present invention is most specific to D-fructose and D-psicose among D- or L-ketohexoses and D- or L-ketopentoses. The enzyme of the present invention can be obtained from microorganisms of the genus *Rhizobium* described later.

The activity of the ketose 3-epimerase of the present invention can be assayed by measuring the amount of D-fructose formed from D-psicose as a substrate. Specifically, the activity of the enzyme can be assayed as follows: A substrate solution is prepared by dissolving D-psicose in 20 mM Tris-HCl buffer (pH 8.0) containing 1 mM $MnCl_2$ to give a final concentration of 1% (w/v). Two milliliters of the substrate solution is admixed with 0.5 ml of the enzyme solution, and the mixture solution is incubated at 45° C. for 30 min. The reaction is stopped by keeping the reaction mixture in boiling water bath for 5 min. Successively, 1 ml of the reaction mixture is admixed with 1 ml of deionized water and 1 ml NADP solution, prepared by dissolving 2.37 g of NADP, 5.93 g of ATP, and 1 g of $MgSO_4$ $7H_2O$ into 500 ml of 0.3 M triethanolamine-HCl buffer (pH 7.6). While, Enzyme solution A and B, described below, were respectively diluted 4-fold with 0.3 M triethanolamine-HCl buffer (pH 7.6) and then both solutions were mixed in equal amount to make into a mixed enzyme solution. Then, 40 ml of the mixed enzyme solution was admixed with the mixture prepared above. After keeping the resulting mixture at room temperature for 30 min, absorbance of the mixture at 340 nm was measured for determining the amount of D-fructose formed by the reaction.

Enzyme solution A: a solution prepared by dissolving 6.7 mg of hexokinase and 82 μl of glucose-6-phosphate dehydrogenase into 0.3 M triethanolamine-HCl buffer (pH 7.6) and filling up with the buffer to give a volume of 2 ml;

Enzyme solution B: a solution prepared by dissolving 4 mg of phosphor-glucose isomerase into 0.3 M triethanolamine-HCl buffer (pH 7.6) and filling up with the buffer to give a volume of 2 ml;

One unit of the enzyme activity is defined as the amount of enzyme which forms 1 μmol-D-fructose/min by epimerizing D-psicose under the above conditions.

The ketose 3-epimerase of the present invention can be prepared by culturing a microorganism of the genus *Rhizobium*, capable of producing the ketose 3-epimerase, and collecting the ketose 3-epimerase formed in the culture broth. For example, *Rhizobium leguminosarum* ATCC14480, *Rhizobium fredii* ATCC35423, *Rhizobium meliloti* ATCC9930, and those mutants can be advantageously used as the microorganism of the genus *Rhizobium*. Among those strains, *Rhizobium leguminosarum* ATCC14480 is preferable to produce the enzyme of the present invention because the strain has a relatively high ability to produce the ketose 3-epimerase As a concrete example of the ketose -epimerase of the present invention, the enzyme having the following physicochemical properties can be used.

(1) Molecular weight
30,000±3,000 daltons when determined on SDS-PAGE;

(2) Optimum pH
pH 9.0 to 9.5 when reacted at 45° C. for 30 min in the presence of 1 mM $Mn^{2+}$ ion;

(3) Optimum temperature
About 50° C. when reacted at pH 8.0 for 30 min in the absence of 1 mM $Mn^{2+}$ ion;
About 650° C. in the presence of 1 mM $Mn^{2+}$ ion;

(4) pH Stability
Stable in a pH range of at least 8 to 10 when incubated at 30° C. for 60 min in the absence of 1 mM $Mn^{2+}$ ion;
Stable in a pH range of pH 4.5 to 9.5 in the presence of 1 mM $Mn^{2+}$ ion;

(5) Thermal stability
Stable below about 50° C. when incubated at pH 8.0 for 10 min in the absence of 1 mM $Mn^{2+}$ ion;
Stable below about 75° C. in the presence of 1 mM $Mn^{2+}$ ion; and (6) Activation by metal ions
Activated by $Mn^{2+}$ and $Mg^{2+}$ ions;

As an example of the ketose 3-epimerase of the present invention, having the above physicochemical properties, may have an amino acid sequence of SEQ ID NO:1 as the N-terminal amino acid sequence.

Usually, the ketose 3-epimerase of the present invention has a prescribed amino acid sequence. For example, an amino acid sequence of SEQ ID NO:2 or that homologous to SEQ ID NO:2 ca be listed. A variant enzyme having an amino acid sequence homologous to SEQ ID NO:2 means an enzyme having an amino acid sequence where one or more amino acids in SEQ ID NO:2 are deleted, replaced or added without altering the enzyme activity of epimerizing the C-3 hydroxyl group of D- or L-ketohexose and forming corresponding D- or L-ketohexose, and epimerizing the C-3 hydroxyl group of D- or L-ketopentose and forming corresponding D- or L-ketopentose. As such a variant enzyme, it is preferable that the enzyme has an amino acid sequence with a homology to SEQ ID NO:2 of, usually, 60% or higher, desirably, 70% or higher, more desirably, 80% or higher, most desirably, 90% or higher.

The term "the DNA of the present invention" means any DNA encoding the above mentioned ketose 3-epimerase. The DNA of the present invention includes a DNA originated from the nature and that synthesized artificially as far as the DNA encodes the ketose 3-epimerase. Microorganisms of the genus *Rhizobium*, including *Rhizobium leguminosarum* (biovar trifolii) ATCC14480, *Rhizobium fredii* ATCC35423, and *Rhizobium meliloti* ATCC9930, can be used as the natural sources of the DNA. A chromosomal DNA containing the DNA of the present invention can be obtained from the cells of these microorganisms. Specifically, a chromosomal DNA containing the DNA can be released extracellularly by the steps of inoculating any of the microorganisms into a nutrient medium, culturing about one to three days under aerobic conditions, collecting the cells from the culture, treating the cells with cell-lytic enzymes such as lysozyme and β-glucanase or with ultrasonication. In addition to the methods described above, use of protein-degrading enzymes such as proteases, detergents such as SDS and freeze-thaw method are also applicable. The objective chromosomal DNA can be obtained from the treated cells by using conventional methods, for example, such as phenol-extraction, alcohol-precipitation, centrifugation, and ribonuclease-treatment. To artificially synthesize the DNA of the present invention, it can be chemically synthesized based on the amino acid sequence of SEQ ID NO:2. PCR-Method is also applicable to obtain the DNA by using a chromosomal DNA containing the DNA as a template and an appropriate chemically synthetic DNA as a primer.

The DNA of the present invention has, usually, a prescribed nucleotide sequence, for example, a nucleotide sequence of SEQ ID NO:3 or a nucleotide sequence homologous to SEQ ID NO:3. A variant DNA, having a homologous nucleotide sequence to SEQ ID NO:3, means that having a nucleotide sequence where one or more nucleotides of SEQ ID NO:3 are deleted, replaced or added without altering the activity of the enzyme encoded thereby. The homology of nucleotide sequence to SEQ ID NO:3 of such a variant DNA is preferable to be , usually, 60% or higher, desirably, 70% or higher, more desirably, 80% or higher, most desirably, 90% or higher. The DNA of the present invention encompasses a DNA having a nucleotide sequence where one or more nucleotides of SEQ ID NO:3 are replaced with other nucleotides without altering the encoded amino acid sequence based on the degeneracy of genetic code.

The DNA of the present invention can be advantageously used for constructing a recombinant DNA by inserting to an appropriate self-replicable vector. Recombinant DNAs are usually constructed by a DNA and a self-replicable vector, and they can be relatively easily prepared by conventional recombinant DNA techniques if the DNA is obtained. Such vectors include, for example, plasmid vectors such as pER322, pUC18, pBluescript II SK(+), pUB110, pTZ4, pC194, pHV14, TRp7, YEp7 and pBS7; and phage vectors such as λgt·λC, λgt·λB, ρ11, φ1 and φ105. To express the DNA of the present invention in $E.\ coli$, pBR322, pUC18, pBluescript II SK (+), λgt·λC and λgt·λB can be preferably used. While, to express the DNA of the present invention in $Bacillus\ subtilis$, pUB110, pTZ4, pC194, ρ11, φ1 and φ105 can be preferably used. Plasmids, pHV14, TRp7, YEp7 and pBS7 are useful in the case of replicating the recombinant DNA in two or more kinds of hosts. In order to insert a DNA into these vectors, conventional methods in the art can be used. Specifically, a DNA is inserted into a vector by the steps of cleaving a chromosomal DNA containing the objective DNA and a self-replicable vector by restriction endonuclease and/or ultrasonication, and ligating the resulting DNA fragment and the resulting vector fragment. The cleavage of the DNA fragment and the vector fragment is easily carried out by using a type II-restriction endonucleases, particularly, such as Sau 3AI, Eco RI, Bin dIII, Barn HI, Sal I, Xba I, Sac I and Pat I. The desired recombinant DNA is obtainable by ligating them in vivo or in vitro using a DNA ligase, optionally, after annealing the both fragments. The recombinant DNA thus obtained is unlimitedly replicable by the steps of introducing into an appropriate host and culturing the resulting transformant.

The recombinant DNA thus obtained can be introduced into an appropriate host-microorganism such as $E.\ coli,\ B.\ subtilis,\ Actinomyces$ and yeasts. The desired transformant can be obtained by applying the colony-hybridization method or by selecting a transformant by the steps of culturing a transformant in nutrient media and selecting a clone which produces the objective ketose 3-epimerase.

A microorganism of the genus $Rhizobium$ or a transformant, capable of producing the ketose 3-epimerase of the present invention, can be cultured using a nutrient medium containing carbon sources, nitrogen sources, inorganic salts, and vitamins for one to five days according to the conventional methods, desirably, in a liquid medium under aerobic conditions by aeration-agitation. The ketose 3-epimerase can be obtained from the cells or culture supernatant of the resulting culture broth. Usually, the culture broth can be used as the crude ketose 3-epimerase. If necessary, the culture broth can be partially purified by conventional methods such as filtration, centrifugation, salting out, dialysis, concentration, freeze-drying, etc. In the case of being required a highly purified enzyme, the ketose 3-epimerase of the present invention can be arbitrarily purified by the combination of, for example, ion-exchange chromatography, gel-filtration chromatography, hydrophobic chromatography, affinity chromatography, high performance liquid chromatography, electrophoresis, adsorption on monoclonal antibody and elution from it. In addition, the ketose 3-epimerase of the present invention or $Rhizobium$ cells expressing the ketose 3-epimerase can be immobilized by conventional methods, and the resulting immobilized enzyme or immobilized cell can be advantageously used for batch reaction or continuous reaction.

In the case of producing the ketose 3-epimerase as a recombinant enzyme, the enzyme may be accumulated intracellularly, depending on the kinds of host microorganisms. In such cases, while the cell or the culture can be used intact, the recombinant enzyme can be advantageously used after extracting it from cells by using osmotic-shock methods or detergents or by disrupting cells using ultrasonication methods or cell-wall digesting enzymes; and separating it from cell or cell debris.

Usually, the conversion reaction of ketose is carried out under the following conditions:
Substrate concentration: 1 to 60% (w/v), desirably, about 5 to 50% (w/v);
Reaction temperature: 10 to 70° C., desirably, about 30 to 60° C.;
pH of the reaction: 5 to 10, desirably, about 7 to 10;
The amount of enzyme: 1 unit of higher/g-substrate, desirably, 50 to 5,000 units/g-substrate; and
Reaction time: Arbitrarily selectable. In the case of batch reaction, 5 to 50 hours be economical reason.

The reaction mixture, thus obtained by the above reaction, contains both material ketose and newly formed ketose, and can be advantageously used intact as sweetener, moisture-retaining agent, crystallization-inhibiting agent, gloss-imparting agent, etc. Usually, the reaction mixture is made into a syrupy product by the decolorization using activated charcoal, the deionization using H- and OH-type ion-exchange resin and the concentration according to the conventional methods.

If necessary, the concentrated syrupy solution can be advantageously subjected to column chromatography using alkaline-metal or alkaline-earth metal type highly acidic cation exchange resin to separate newly formed ketose and material ketose. The resulting newly formed ketose high content fraction can be concentrated to make into a syrupy product. In the case of the ketose can be crystallized, a crystalline product ca be advantageously obtained by the crystallization. The separated material ketose can be used again as a material for the conversion.

The ketose, thus obtained, is preferable as a sweetener and can be advantageously used for sweetening or improvement of preference of foods and beverages, feeds, baits, and various products for orally administration such as tooth paste, cachou, sublingual tablet, and oral medicine.

The following experiments explain the present invention in detail. In the following experiments, D-psicose 3-epimerase activity, converting D-psicose into D-fructose, was assayed according to the aforementioned assay method and expressed as ketose 3-epimerase activity.

EXPERIMENT 1

Cultivation of $Rhizobium\ leguminosarum$ ATCC14480

A liquid culture medium consisting of 1.5% (w/v) of "PINE-DEX #4", a partial starch hydrolyzate commercialized by Matsutani Chemical Industries Co., Ltd., Hyogo, Japan, 0.1% (w/v) of "SUNMALT S", a maltose product commercialized by Hayashibara Shoji, Inc., Okayama, Japan, 0.1% (w/v) of "YEAST EXTRACT S", a yeast extract commercialized by Nihon Pharmaceutical Co., Ltd., Tokyo, Japan, 0.5% (w/v) of "POLYPEPTONE S", a yeast extract commercialized by Nihon Pharmaceutical Co., Ltd., Tokyo, Japan, 0.1% (w/v) of dipotassium phosphate, 0.06% (w/v) of sodium di-hydrogen phosphate, 0.05% (w/v) of magnesium sulfate, 0.001% (w/v) of ferrous sulfate, 0.001% of manganese sulfate, and water was placed in a 30 L-jar fermenter in an amount of 20 L, sterilized by autoclaving at 120° C. for 20 min. Successively, the culture medium was inoculated with 1% of seed culture of *Rhizobium leguminosarum* ATCC14480, and followed the cultivation under aeration-agitation conditions at 27° C. for 72 hours. The ketose 3-epimerase activity of the resulting culture broth was about 1.0 unit/ml-broth.

EXPERIMENT 2

Purification of a Ketose 3-epimerase

About 10 L of the culture broth obtained in Experiment 1 was centrifuged to collect cells. The resulting cells were suspended in 1 L of 20 mM Tris-HCl buffer (pH 8.0) and disrupted using "DYNO®-MILL", a beads mill commercialized by W. A. Bechofen GmBH, Germany. The resulting disrupted cell-suspension was centrifuged and the supernatant was collected as a cell-free extract. After dialyzing the cell-free extract against 20 mM Tris-HCl buffer (pH 8.0), the resulting crude enzyme solution was subjected to anion-exchange column chromatography using 800 ml of "SEPA-BEADS FP DA-13" gel, an anion-exchange gel commercialized by Mitsubishi Chemical Corporation, Tokyo, Japan, and the absorbed ketose 3-epimerase was eluted with a linear gradient increasing from 0 M to 0.6 M of sodium chloride. The active fractions were collected and added ammonium sulfate to give a final concentration of 1 M, and then subjected to hydrophobic column chromatography using 100 ml of "BUTYL-TOYOPEARL 650M" gel, a gel commercialized by Tosoh Corporation, Tokyo, Japan. The ketose 3-epimerase was not adsorbed on the gel and eluted in non-absorbed fractions. The active fractions were collected and dialyzed against 20 mM Tris-HCl buffer (pH 8.0), and then subjected to anion-exchange column chromatography using 100 ml of "DEAE-TOYOPEARL 650M" gel, a gel commercialized by Tosoh Corporation, Tokyo, Japan. The absorbed ketose 3 -epimerase was eluted with a linear gradient increasing from 0 M to 0.6 M of sodium chloride. The active fractions were concentrated and then subjected to gel-filtration chromatography using 300 ml of "TOYOPEARL HW-55S", a gel commercialized by Tosoh Corporation, Tokyo, Japan. The active fraction was further purified by subjecting to hydrophobic column chromatography, anion-exchange column chromatography, and gel-filtration chromatography, using "RESOURCE PHE", "RESOURCE Q", "SUPERDEX 200 HR26/60", pre-packed columns commercialized by Amasham Bioscience, and a purified preparation of the ketose 3-epimerase was obtained. The results of the purification are summarized in Table 1.

TABLE 1

| Purification step | Ketohexose 3-epimerase activity* (units) | Specific activity of ketohexose 3-epimerase (units/mg-protein) | Yield (%) |
| --- | --- | --- | --- |
| Cell extract | 5,010 | 0.02 | 100 |
| Eluate from "SEPABEADS" | 6,060 | 0.13 | 121 |
| Eluate from "BUTYL-TOYOPEARL" | 2,850 | 0.17 | 57 |
| Eluate from "DEAE-TOYOPEARL" | 2,350 | 0.31 | 47 |
| Eluate from "TOYOPEARL HW-55S" | 1,020 | 0.51 | 20 |
| Eluate from "RESOURCE PHE" | 610 | 3.5 | 12 |
| Eluate from "RESOURCE Q" | 270 | 10.3 | 5 |
| Eluate from "SUPERDEX 200" | 90 | 41.6 | 2 |

*D-Psicose 3-epimerase activity

As is evident from the results in Table 1, the specific activity of the enzyme increased about 2,080-fold by the purification. The finally purified enzyme preparation of ketose 3-epimerase was assayed for purify on gel electrophoresis using a 5-20%- (w/v) gradient polyacrylamide gel and detected on the gel as a single protein band, i.e. a high purity preparation.

EXPERIMENT 3

Properties of Ketose 3-epimerase

EXPERIMENT 3-1

Molecular Weight

The purified enzyme preparation of ketose 3-epimerase, obtained by the method in Experiment 2, was subjected to SDS-PAGE using a 5-20% (w/v) gradient gel and the molecular weight of the was measured comparing with molecular weight markers, commercialized by Bio-Rad Japan, Tokyo, Japan. It was revealed that the ketose 3-epimerase has a molecular weight of 30,000±3,000 daltons.

EXPERIMENT 3-2

Optimum pH and Optimum Temperature

Effects of pH or temperature on the ketose 3-epimerase activity were investigated using the purified enzyme preparation of ketose 3-epimerase, obtained by the method in Experiment 2, according to the as say method. The results are in FIG. 1 (Optimum pH) and in FIG. 2 (Optimum temperature), respectively. It was revealed that the optimum pH of the ketose 3-epimerase of the present invention was 9.0 to 9.5 when reacted at 45° C. for 30 min in the presence of 1 mM $Mn^{2+}$ ion, and the optimum temperature of the enzyme was about 50° C. when reacted at pH 8.0 for 30 min in the absence of 1 mM $Mn^{2+}$ ion (● in FIG. 2), and about 65° C. in the presence of 1 mM $Mn^{2+}$ ion (○ in FIG. 2).

EXPERIMENT 3-3 pH Stability and Thermal Stability pH Stability and thermal stability of the enzyme were investigated using the purified enzyme preparation of ketose 3-epimerase, obtained by the method in Experiment 2. pH Stability of the enzyme was determined by the steps of incubating the enzyme solution in 10 mM buffer at various pHs in the presence or absence of 1 mM $MnCl_2$, and at 30° C. for 60 min, adjusting the pH to 8.0, and measuring the residual enzyme activity. Thermal stability of the enzyme was determined by the steps of incubating enzyme in 20 mM Tris-HCl buffer (pH 8.0) under various temperatures for 60 min in the presence or absence of 1 mM $MnCl_2$, cooling in water, and measuring the residual enzyme activity. The results are in FIG. 3 (pH Stability) and in FIG. 4 (Thermal stability) respectively. As is evident from the results in FIG. 3, it was revealed that the ketose 3-epimerase of the present invention was stable in the range of at least pH 8 to 10 in the absence of 1 mM $Mn^{2+}$ ion (● in FIG. 3). Since the determination of formed D-fructose is inhibited in the pH higher than 10 in the assay, the pH stability of the enzyme in the range of pH higher than 10 could not be measured. It was also revealed that the enzyme is stable in the range of pH 4.5 to 9.5 in the presence of 1 mM $Mn^{2+}$ ion (○ in FIG. 3). As is evident from the results in FIG. 4, it was revealed that the ketose 3-epimerase of the present invention is stable below about 50° C. in the absence of $Mn^{2+}$ ion (● in FIG. 4), and below about 75° C. in the presence of 1 mM $Mn^{2+}$ ion (○ in FIG. 4).

EXPERIMENT 3-4

Effects of Metal Ions on the Enzyme Activity

Effects of metal ions on the enzyme activity were investigated using the purified enzyme preparation of ketose 3-epimerase, obtained by the method in Experiment 2, and substrate solutions without 1 mM $MnCl_2$ in the presence of 1 mM of various metal ions according to the assay method. Among the metal salts, two ferrous chloride ($FeCl_2$ and $FeCl_3$) and mercury chloride ($HgCl_2$) inhibit the determination of D-fructose in the reaction mixture. Accordingly, the determination of D-fructose in the three kinds of metal salt was carried out using HPLC. The results are in Table 2.

TABLE 2

| Metal salt | Relative activity (%) | Metal salt | Relative activity (%) |
|---|---|---|---|
| None | 100 | $MgCl_2$ | 141 |
| $AlCl_3$ | 86 | $MnCl_2$ | 283 |
| $BaCl_2$ | 96 | $NiCl_2$ | 64 |
| $CaCl_2$ | 89 | $PbCl_2$ | 69 |
| $CoCl_2$ | 101 | $SrCl_2$ | 103 |
| $CuCl_2$ | 60 | $SnCl_2$ | 114 |
| $FeCl_2$* | 67 | $ZnCl_2$ | 13 |
| $FeCl_3$* | 64 | EDTA | 97 |
| $HgCl_2$* | 35 | | |

*The amount of D-fructose was determined by HPLC.

Among 15 kinds of metal ions tested, the activity of the ketose 3-epimerase of the present invention was activated by $Mg^{2+}$ and $Mn^{2+}$ ions to about 140% and about 280%, respectively, in comparison with the case without metal ions. The activity was slightly activated by $Sn^{2+}$ ion, but not activated by $Co^{2+}$ and $Sr^{2+}$ ions. The activity was slightly inhibited by Ni2+, $Cu^{2+}$, $Pb^{2+}$, $Fe^{2+}$, and $Fe^{3+}$ ions, and remarkable inhibited by $Zn^{2+}$ and $Hg^{2+}$ ions. The activity was not inhibited by EDTA.

EXPERIMENT 3-5

N-terminal Amino Acid Sequence

N-terminal amino acid sequence of the enzyme was determined using the purified enzyme preparation of ketose 3-epimerase, obtained by the method in Experiment 2, using "MODEL 429HT", a protein sequencer commercialized by Applied Biosystems Japan, Tokyo, Japan. As a result, it was revealed that the enzyme had the N-terminal amino acid sequence of SEQ ID NO: 1, i.e., Met-Glu-Gly-Phe-Gly-Val-His-Thr-Ser-Met.

EXPERIMENT 4

Cloning of a DNA Encoding the Ketose 3-epimerase and Preparation of a Recombinant DNA Comprising the DNA and a Transformant A DNA encoding the ketose 3-epimerase was cloned from *Rhizobium leguminosarum* ATCC14480, and a self-replicable recombinant DNA containing the DNA was constructed. Successively, the nucleotide sequence of the DNA encoding the enzyme was determined and a transformant was also prepared.

EXPERIMENT 4-1

Preparation of Chromosomal DNA

A liquid culture medium (pH 7.0) consisting of 2.0% (w/v) of D-mannitol, 0.1% (w/v) of "BACT-YEAST EXTRACT", a yeast extract commercialized by DIFCO International, Netherlands, 0.5% (w/v) of "BACT-PEPTONE", a peptone commercialized by DISCO International, Netherlands, 0.1% (w/v) of dipotassium phosphate, 0.1% (w/v) of sodium phosphate di-hydrate, 0.05% (w/v) of magnesium sulfate heptahydrate, and water was placed in 20 Erlenmeyer flasks with a volume of 500 ml in a respective amount of 50 ml, sterilized by autoclaving at 121° C. for 20 min, cooled and inoculated with *Rhizobium leguminosarum* ATCC14480, followed by the cultivation under rotary-shaking conditions at 27° C. and 230 rpm for 2 days.

The cells collected from the culture by centrifugation were suspended in TES buffer (pH 8.0), the suspended solution was admixed with lysozyme to give a concentration of 0.05% (w/v), and incubated at 37° C. for 30 min. After freezing the lysate at −80° C. for one hour, the lysate was added with TES buffer (pH 9.0) and heated to 60° C. The solution was added with a mixture of TES buffer and phenol, and was vigorously shaken for 10 min in an ice bath, and the supernatant was collected by centrifugation. The supernatant was added twice volume of cold ethanol, and resulting precipitate was collected as a crude chromosomal DNA. The crude chromosomal DNA was dissolved in SSC buffer (pH 7.1), and admixed with 7.5 μg of ribonuclease and 125 μg of proteinase, and incubated at 37° C. for one hour. The chromosomal DNA was extracted from the reactant by adding chloroform/isoamylalcohol mixture, then, admixed with cold ethanol, and the resulting precipitate containing chromosomal DNA was collected. The purified chromosomal DNA, obtained according to the method described above, was dissolved in SSC buffer (pH 7.1) to give a concentration of about one mg/ml and frozen at −80° C.

EXPERIMENT 4-2

Cloning of a DNA Encoding the Ketose 3-epimerase and Determination of the Nucleotide Sequence of the DNA Based on the N-terminal amino acid sequence of the ketose 3-epimerase, i.e., SEQ ID NO: 1, obtained in Experiment 3-5, a protein having an amino acid sequence homologous to the amino acid sequence was searched from a data base, "Gen-Bank", using a homology search program, "BLAST". As a result, a unknown protein from *Sinorhizobium meliloti* 1021, having an amino acid sequence of 9 per 10 amino acids are identical to the N-terminal amino acid sequence, and the unknown protein was deduced to a saccharide epimerase. It was found that the unknown protein has the amino acid sequence of SEQ ID NO: 4 and is encoded by a DNA having a nucleotide sequence of SEQ ID NO: 5. Based on the premise that the amino acid sequence of the ketose 3-epimerase from *Rhizobium leguminosarum* ATCC14480 shows a high homology to the amino acid sequence of the unknown protein in a whole region, the cloning of a DNA encoding the ketose 3-epimerase was started.

Based on the 10th to 16th amino acid sequence of SEQ ID NO: 4 which is the amino acid sequence of the unknown protein from *Sinorhizobium meliloti* 1021, an oligonucleotide having the nucleotide sequence of SEQ ID NO: 6 was synthesized as a sense primer. Also, based on the 179th to 185th amino acid sequence of SEQ ID NO:4, an oligonucleotide having the nucleotide sequence of SEQ ID NO:7 was synthesized as an anti-sense primer. Using the primers, PCR-amplification was carried out by using the chromosomal DNA obtained in Experiment 4-1 as a template. As a result, a DNA fragment of about 600 bp was amplified. The resulting DNA fragment was inserted to the Srf I site of pCR-Script Amp SK+, a cloning vector commercialized by Stratagene (Now, Agilent Technologies, Inc, US), and the resulting recombinant DNA was used for the transformation of *E. coli* JM109. Plasmids prepared from 5 clones selected from the resulting transformants were analyzed, revealing that all clones have the objective DNA fragment of about 600 bp. One clone was selected and the recombinant plasmid was named as "pCR12-1".

The nucleotide sequence of the DNA fragment of about 600 bp in the recombinant DNA, pCR12-1, was determined by conventional dideoxy-method. The amino acid sequence encoded by the determined 345 bp-nulceotide sequence showed a high homology, about 78%, to the partial amino acid sequence of the unknown protein from *Sinorizobium meliloti* 1021, which is deduced to be a saccharide epimerase. From the result, it was presumed that the obtained DNA fragment is a part of the DNA encoding the objective ketose 3-epimerase.

Before the next experiment, it was confirmed that the DNA fragment deduced to be a part of DNA encoding ketose 3-epimerase is not cleaved by the restriction endonuclease, Cla I. The chromosomal DNA obtained in Experiment 4-1 was digested with Cla I, and the resulting digests were self-ligated to make into cyclized DNAs. Based on the nucleotide sequence of the DNA fragment, deduced to be a part of DNA encoding ketose 3-epimerase; oligonucleotides having the nucleotide sequences of SEQ ID NOs: 8 to 11 were synthesized as primers. First PCR was carried out using the oligonucleotises having the nucleotide sequence of SEQ ID NOs: 8 and 9 as sense and anti-sense primer, respectively, and the above cyclized DNAs as templates. Successively, 2nd PCR was carried out using the oligonucleotides having the nucleotide sequence of SEQ ID NOs: 10 and 11 as sense and anti-sense primer, respectively. As a result, a DNA fragment of about 1,800 bp was amplified.

The nucleotide sequence of the DNA fragment of about 1,800 bp, obtained by the above method, was directly determined by the conventional dideoxy-method. Then, the N-terminal amino acid sequence of the ketose 3-epimerase i.e., SEQ ID NO:1, determined by the method in Experiment 3-5, was compared with the amino acid sequence encoded by the nucleotide sequence. As a result, the N-terminal amino acid sequence was completely identical to the first to the 10th amino acid sequence in SEQ ID NO: 2 encoded by the nucleotide sequence. The result indicates that the ketose 3-epimerase from *Rhizobium leguminosarum* ATCC14480 is consisted of 282 amino acid residues represented by SEQ ID NO:2, and the DNA encoding the enzyme is consisted of 846 bp represented by SEQ ID NO:3. The molecular weight calculated from the amino acid sequence of SEQ ID NO: 2 was about 30,900 daltons, and the value gave close agreement with the molecular weight of the ketose 3-epimerase from *Rhizobium leguminosarum* ATCC14480, determined to be 30,000±3,000 daltons in Experiment 3.

EXPERIMENT 4-3

Re-cloning of a DNA Encoding Ketose 3-epimerase and Confirmation of the Base Sequence In order to confirm the nucleotide sequence of the DNA encoding the ketose 3-epimerase, which was determined in Experiment 4-2, the following experiment was carried out. Two primers, having the nucleotide sequences of initial and stop codon of the DNA, were synthesized, and the DNA encoding the ketose 3-epimerase was re-amplified by PCR-method using the above primers and the chromosomal DNA obtained in Experiment 4-1 as a template. The resulting amplified DNA fragment was re-cloned and the nucleotide sequence was determined. In order to insert the DNA encoding the ketose 3-epimerase to an expression vector, the above primers were designed to introduce Nde I site at the upstream of the DNA and Eco RI site at the downstream of the DNA.

Two oligonucleotides, having SEQ ID NOs: 12 and 13, were synthesized, respectively. Then, a DNA fragment was amplified by PCR method using the chromosomal DNA, obtained in Experiment 4-1, as a template and the above two oligonucleotides as a sense primer and an anti-sense primer. The resulting amplified DNA fragment was inserted in Srf I site of a vector, pCR-Script Amp SK+, commercialized by Stratagene (Now, Agilent Technologies, Inc, US); and the resulting recombinant DNA was named as "pCRDPE6". The nucleotide sequence of the DNA in pCRDPE6 was determined by conventional dideoxy-method. As the result, it was revealed that the DNA has the identical nucleotide sequence with SEQ ID NO:3 determined in Experiment 4-2.

EXPERIMENT 5

Construction of a Recombinant DNA, pETDPE1, for Expressing the Ketose 3-epimerase and the Production of the Recombinant Ketose 3-epimerase by the Transformant The DNA encoding the ketose 3-epimerase in the recombinant DNA, pCRDPE6, was inserted into an expression vector. The recombinant ketose 3-epimerase was expressed in *E coli* and the activity was assayed.

EXPERIMENT 5-1

Construction of a Recombinant DNA, pETDPE1, for Expressing Ketose 3-epimerase and Preparation of a Transformant, ETDPE1

The recombinant DNA, pCRDPE6, comprising the DNA encoding the ketose 3-epimerase, obtained in Experiment 4-3, was digested with restriction endonucleases, Nde I and Eco RI, and then the restriction endonucleases were inactivated by heating at 70° C. for 30 min. The resulting digested DNA was inserted to a expression vector, pET-38b (+), commercialized by Novagen (Now, Merck Chemicals Ltd., Germany), using "LIGATION KIT VER. 2.1", a kit commercialized Takara Shuzo Co., Ltd., Kyoto Japan. *E. coli* JM109, commercialized by Toyobo Co., Ltd., Osaka, Japan, was transformed by using the resulting product, and a transformant having the objective recombinant DNA was selected from the transformants. The objective recombinant DNA was isolated from the transformant and named as "pETDPE1". Then, pETDPE1 is shown in FIG. 5. A transformant, ETDPE1, was prepared by transforming "*E. coli* Rosetta (DE3)", a host *E. coil* commercialized by Novagen (Now, Merck Chemicals Ltd., Germany), with pETDPE1.

EXPERIMENT 5-2

Production of the Recombinant Ketose 3-epimerase using the Transformant ETDPE1

A liquid culture medium consisting of 10 g/L of "BACTO-TRYPTONE", a tryptone commercialized by Difco International, Netherlands, 5 g/L of "BACTO-YEAST EXTRACT", a yeast extract, commercialized by Difco International, Netherlands, 10 g/L of sodium chloride, and water was placed in a 500 ml-Erlenmeyer flask in a amount of 100 ml, sterilized by autoclaving at 121° C. for 20 min, and cooled. Then, the liquid medium was sterilely set to pH 7.5, and sterilely admixed with 2 mg of kanamycin. The transformant, ETDPE1, obtained by the method in Experiment 5-1, was inoculated into the above liquid medium, and cultured at 37° C. under aeration-agitation conditions. Then, isopropyl-1-thio-β-D-galactopyranoside (IPTG) was added to the culture to give a final concentration of 0.4 mM, at the point that the turbidity of the culture was reached to about 0.6, to induce the expression of the ketose 3-epimerase gene, and the cultivation was further continued at 27° C. for 3 hours. Cells were collected from the culture broth by conventional centrifugation. Successively, cells were suspended in 20 mM Tris-HCl buffer (pH 7.5), and were disrupted in an ice bath using "Model UH-600", a ultrasonic homogenizer commercialized by MST Corporation, Aichi, Japan, and the supernatant obtained by centrifuging the homogenate was used as a soluble fraction of cell homogenate.

The ketose 3-epimerase activity of the soluble fraction of cell homogenate, prepared as described above, was assayed, and the value was expressed in terms of the activity/ml-culture. As a control, E. coli Rosetta (DE3), having a plasmid vector, pET-38b (+), was cultured using the same conditions with the above transformant, and the ketose 3-epimerase activity was assayed after preparing the soluble fraction of cell homogenate in the same manner. The results are in Table 3.

TABLE 3

| Strain | Ketose 3-epimerase activity (units/ml-broth) |
|---|---|
| ETDPE1 (Present invention) | 8.7 |
| E. coli Rosetta (DE3) pET-38b (+) (Control) | —* |

*Not detected.

As is evident from the results in Table 3, it was revealed that the transformant ETDPE1 produced the recombinant ketose 3-epimerase intracellularly. In the case of the control E. coli having the expression vector only, no enzyme activity was detected.

According to the methods described in Experiment 2, the soluble fraction of cell homogenate, obtained by the method in Experiment 5, was partially purified by salting out, dialysis and successive column chromatographies on "SEPA-BEADS" gel and "BUTYL-TOYOPEARL" gel, and the partially purified enzyme preparation was analyzed according to the methods in Experiment 3. As the results, the recombinant ketose 3-epimerase showed the following enzymatic properties:

The optimum pH : pH 9.0 to 9.5 when reacted at 45° C. for 30 min in the presence of 1 mM $Mn^{2+}$ ion;
The optimum temperature : About 65° C. when reacted at pH 8.0 for 30min in the presence of 1 mM $Mn^{2+}$ ion;
pHStability: Stable in a range of about pH 4.5 to 9.5 when incubated at various pHs at 30° C. for 60 min in the presence of 1 mM $Mn^{2+}$ ion;
Thermal stability : Stable up to about 50° C. when incubated at various temperatures at pH 8.0 for 10 min in the absence of 1 mM $Mn^{2+}$ ion;
Stable up to about 75° C. in the presence of 1 mM $Mn^{2+}$ ion;
Those enzymatic properties of the recombinant enzyme were substantially identical to those of the enzyme prepared by the methods in Experiment 2. The results described above indicate that the ketose 3-epimerase of the present invention can be advantageously produced by recombinant DNA techniques.

EXPERIMENT 6

Substrate Specificity of Ketose 3-epimerase

By using the purified preparation of the ketose 3-epimerase, obtained by the method in Experiment 2, the substrate specificity of the enzyme was investigated using various D- or L-ketohexoses and D- or L-ketopentoses as substrates. Substrate solutions were prepared by dissolving D-fructose, D-psicose, D-tagatose, D-sorbose, D-xylulose, D-ribulose, L-fructose, L-psicose, L-tagatose, L-sorbose, L-xylulose, or L-ribulose into 20 mM Tris-HCl buffer (pH 8.0) containing 1 mM MnCl2 to give a final concentration of 1% (w/v), respectively. Then, each substrate solution was further admixed with 2 units/g-substrate or 20 units/g-substrate, on a dry solid basis, as D-psicose 3-epimerase activity of the purified preparation of the ketose 3-epimerase, obtained by the method in Experiment 2; and followed by the enzyme reaction at 45° C. for 17 hours. After stopping the reaction by keeping the reaction mixture at 100° C. for 10 min, the content of epimer formed from each substrate was measured using high performance liquid chromatography (hereinafter, abbreviated as "HPLC"). HPLC was carried out under the following conditions:
Column: MCI GEL CK08EC, commercialized by Mitsubishi Chemical Corporation, Tokyo, Japan;
Eluent: water;
Column temperature: 75° C.
Flow rate: 0.6 ml/min
Detection: RID-10A, a differential refractometer commercialized by Shimadzu Corporation, Kyoto, Japan;
The results are in Table 4.

TABLE 4

| | | | Epimer content in the reaction products (%) | |
|---|---|---|---|---|
| | | | The amount of enzyme (units/g-substrate) | |
| Substrate | | Formed epimer | 2 | 20 |
| D-Ketohexose | D-Fructose | D-Psicose | 17.7 | 25.8 |
| | D-Psicose | D-Fructose | 39.4 | 74.1 |
| | D-Tagatose | D-Sorbose | 0.6 | 5.3 |
| | D-Sorbose | D-Tagatose | 0 | 0.1 |
| D-Ketopentose | D-Xylulose | D-Ribulose | 2.3 | 19.6 |
| | D-Ribulose | D-Xylulose | 17.1 | 43.4 |
| L-Ketohexose | L-Fructose | L-Psicose | 0 | 1.4 |
| | L-Psicose | L-Fructose | 1.6 | 11.3 |
| | L-Tagatose | L-Sorbose | 3.2 | 26.7 |
| | L-Sorbose | L-Tagatose | 0 | 6.2 |
| L-Ketopentose | L-Xylulose | L-Ribulose | 1.6 | 10.3 |
| | L-Ribulose | L-Xylulose | 19.2 | 58.4 |

As is evident from the results in Table 4, it was revealed that the ketose 3-epimerase of the present invention acts on all tested D- or L-ketohexose and D- or L-ketopentose, and epimenize anomer of the C-3 hydroxyl group to form corresponding D- or L-ketohexose and D- or L-ketopentose in varying degrees. In the case of using a small amount of enzyme, i.e., 2 units/g-substrate, about 39% of D-psicose was converted into D-fructose, and about 18% of D-fructose was converted into D-psicose. Therefore, it was revealed that the ketose 3-epimerase of the present invention most efficiently catalyzes the conversion of D-fructose into D-psicose and vice versa. Also, the enzyme efficiently catalyzed the conversion of D-ribulose into D-xylulose and vice versa, and L-ribulose into L-xylulose and vice versa. However, the enzyme slightly catalyzed the conversion of D-tagatose into D-sorbose and vice versa.

According to the above method, the action of the enzyme on D-aldohexoses and D- or L-aldopentoses was investigated, and it was revealed that the ketose 3-epimerase does not act on those substrates. It was confirmed that the enzyme does not act on aldoses used in the investigation.

EXPERIMENT 7

Ketose 3-epimerases from other Microorganisms of the Genus *Rhizobium*

*Rhizobium fredii* ATCC35423 and *Rhizobium meliloti* ATCC9930, being capable of producing ketose 3-epimerase among other microorganisms of the genus *Rhizobium*, were cultured respectively in a fermenter as in the case of Experiment 1. Partially purified enzymes were respectively prepared by the steps of disrupting cells, collecting the supernatant of cell homogenate, dialyzing, and subjecting to anion exchange column chromatography using about 10 liters of culture broth as in the case of Experiment 2. The enzymatic properties of the resulting partially purified enzymes were investigated as in the case of Experiment 3. The results were summarized in Table 5 with the enzymatic properties of the ketose 3-epimerases from aforesaid *Rhizobium leguminosarum* ATCC14480 and from heretofore known *Pseudomonas cichorii* ST-24 (abridgement from Ken Izumori et al., Biosci. Biotech. Biochem., 57, 1037-1039 (1993)).

TABLE 5

| | Enzymatic properties | | | |
|---|---|---|---|---|
| Microorganism | Optimum pH | Optimum Temp. | pH Stability | Thermal Stability |
| *Rhizobium fredii* ATCC35423 | 9.0-9.5* | 50° C. (65° C.)* | 8.0-10.0** | Below 50° C. (Below 75° C.)* |
| *Rhizobium meliloti* ATCC9930 | 9.0-9.5* | 55° C. (65° C.)* | 8.0-10.0** | Below 50° C. (Below 75° C.)* |
| *Rhizobium leguminosarum* ATCC14480 | 9.0-9.5* | 50° C. (65° C.)* | 8.0-10.0** | Below 50° C. (Below 75° C.)* |
| *Pseudomonas cichorii* ST-24 | 7.0-9.0 | About 60° C. | 5.0-8.0 | Below 50° C. |

*In the presence of 1 mM $Mn^{2+}$ ion
**Stable at least in the range of pH 8.0-10.0. Stability in the range of pH higher than 10 was not tested.

As is evident from the results in Table 5, ketose 3-epimerases from *Rhizobium fredii* ATCC35423 and *Rhizobium meliloti* ATCC9930 showed almost the same enzymatic properties with those of the enzyme from *Rhizobium leguminosarum* ATCC14480. Enzymatic properties of the ketose 3-epimerases from microorganisms of the genus *Rhizobium* were different from those of the enzyme from well-established *Pseudomonas cichorii* ST-24.

Substrate specificities of ketose 3-epimerases from *Rhizobium fredii* ATCC35423 and *Rhizobium meliloti* ATCC9930 were respectively investigated as in the case of Experiment 6 using partially purified enzymes purified to the level of the step of DEAE-TOYOPEARL as described in Experiment 2. The substrate specificities of the enzymes were almost the same with the case of the ketose 3-epimerase from *Rhizobium leguminosarum* ATCC14480.

The following examples explain the present invention in detail. However, the present invention is not restricted by them. The ketose 3-epimerase activity in the following examples is expressed by D-psicose 3-epimerase activity as in the cases of Experiments.

EXAMPLE 1

Preparation of a Ketose 3-epimerase

The liquid culture medium, with the same composition with that used in Experiment 1, was placed in a 30-L fermenter in an amount of about 20 L and sterilized by heating at 120° C. for 20min. Then, 1% (v/v) of a liquid medium of the seed culture of *Rhizobium fredii* ATCC35423 was inoculated into the liquid culture medium, and the bacterium was cultured at 27° C. for 60 hours under aeration-agitation conditions. The ketose 3-epimerase activity of the culture broth was about 0.7 unit/ml-broth. Cells were collected from about 18 L of the culture broth by centrifuging, suspended in 1.5 L of 20 mM Tris-HCl buffer (pH 8.0), and disrupted using "DYNO®-MILL", a beads mill commercialized by W. A. Bechofen GmBH, Germany. The resulting disrupted cell suspension was centrifuged to collect the supernatant as cell-free extract. According to the method in Experiment 2, the cell-free extract was partially purified to the step of anion-exchange column chromatography using "DEAE-TOYOPEARL650S" commercialized by Tosoh Corporation, Tokyo, Japan. As a result, total activity of about 7,200 units of partially purified ketose 3-epimerase was obtained.

EXAMPLE 2

Preparation of a Ketose 3-epimerase

According to the conventional method, *Rhizobium leguminosarum* ATCC 14480 was mutated and a mutant capable of producing the ketose 3-epimerase in higher amount was obtained. The liquid culture medium, with the same composition with that used in Experiment 1, was placed in a 30-L fermenter in an amount of about 20 L and sterilized by heating at 120° C. for 20min. Then, 1% (v/v) of a liquid medium of the seed culture of the above mutant was inoculated into the liquid culture medium, and the bacterium was cultured at 27° C. for 60 hours under aeration-agitation conditions. The ketose 3-epimerase activity of the culture broth was about 13 units/ml-broth. Cells were collected from about 18 L of the culture broth by centrifuging, suspended in 1.5 L of 20 mM Tris-HCl buffer (pH 8.0), and disrupted using "DYNO®-MILL", a beads mill commercialized by W. A. Bechofen GmBH Germany. The resulting disrupted cell suspension was centrifuged to collect the supernatant as cell-free extract. According to the method in Experiment 2, the cell-free extract was partially purified to the step of anion-exchange column chromatography using "DEAE-TOYOPEARL 650S", commercialized by Tosoh Corporation, Tokyo, Japan. As a result, total activity of about 82,000 units of partially purified ketose 3-epimerase was obtained.

EXAMPLE 3

Production of D-psicose from D-fructose

To a 10% (w/v) D-fructose aqueous solution (pH8.0, containing 1 mM $MnCl_2$), 50 units/g-D-fructose of the partially purified ketose 3-epimerase from *Rhizobium fredii*

ATCC35423, obtained by the method in Example 1, was added and followed the reaction at 45° C. for 30 hours. After the reaction, the reaction mixture was decolorized using activated charcoal, desalted using "DIAION SK1B", a H-form ion-exchange resin commercialized by Mitsubishi Chemical Corporation, Tokyo, Japan, and "DIAION WA30", a OH-form ion-exchange resin, commercialized by Mitsubishi Chemical Corporation, Tokyo, Japan, and concentrated under reduced pressure to make into a clear syrup comprising D-psicose. The syrup was purified by subjecting to column chromatography using Na-form "AMBERLITE CR-1310", a slat-form strongly acidic cation-exchange resin commercialized by Organo Corporation, Tokyo, Japan and the resulting D-psicose fraction was concentrated; and then a syrupy D-psicose was obtained in a yield of about 23%, on a dry solid basis. The physicochemical properties of the product were identical with those of the standard D-psicose. The product can be advantageously used as sweetener, carbon source for fermentation, reagent, chemical, material or intermediate for pharmaceuticals, etc. Since the reaction is reversible, D-fructose can be easily produced by using D-psicose as the material.

EXAMPLE 4

Preparation of D-ribulose from D-xylulose

To a 1% (w/v) D-xylulose aqueous solution (pH8.0, containing 1 mM $MnCl_2$), 20 units/g-D-xylulose of the ketose 3-epimerase from *Rhizobium leguminosarum* ATCC14480, partially purified to the step of DEAE-TOYOPEARL by the method in Experiments 1 and 2, was added and followed the reaction at 45° C. for 50 hours. After the reaction, the reaction mixture was decolorized, desalted and concentrated under reduced pressure as in the case of Example 3 to make into a clear syrup comprising D-ribulose. The syrup was purified by subjecting to column chromatography using the slat-form strongly acidic cation-exchange resin as in the case of Example 3, and the resulting D-ribulose fraction was concentrated; and then a syrupy D-ribulose was obtained in a yield of about 16%, on a dry solid basis. The physicochemical properties of the product were identical with those of the standard D-ribulose. The product can be advantageously used as sweetener, carbon source for fermentation, reagent, chemical, material or intermediate for pharmaceuticals, etc. Since the reaction is reversible, D-xylulose can be easily produced by using D-ribulose as the material.

EXAMPLE 5

Preparation of L-ribulose from L-xylulose

To a 1% (w/v) L-xylulose aqueous solution (pH8.0, containing 1 mM $MnCl_2$), 100 units/g-L-xylulose of the partially purified ketose 3-epimerase from *Rhizobium fredii* ATCC35423, obtained by the method in Example 1, was added and followed the reaction at 45° C. for 50 hours. After the reaction, the reaction mixture was decolorized, desalted and concentrated under reduced pressure as in the case of Example 3 to make into a clear syrup comprising L-ribulose. The syrup was purified by subjecting to column chromatography using the slat-form strongly acidic cation-exchange resin as in the case of Example 3, and the resulting L-ribulose fraction was concentrated; and then a syrupy L-ribulose was obtained in a yield of about 25%, on a dry solid basis. The physicochemical properties of the product were identical with those of the standard L-ribulose. The product can be advantageously used as sweetener, carbon source for fermentation, reagent, chemical, material or intermediate for phar- maceuticals, etc. Since the reaction is reversible, L-xylulose can be easily produced by using L-ribulose as the material.

EXAMPLE 6

Preparation of L-sorbose from L-tagatose

To a 1% (w/v) L-tagatose aqueous solution (pH8.0, containing 1 mM $MnCl_2$), 20 units/g-L-tagatose of the partially purified ketose 3-epimerase from the mutant of *Rhizobium leguminosarum* ATCC14480 capable of producing the enzyme in high amount, obtained by the method in Example 2, was added and followed the reaction at 45° C. for 50 hours. After the reaction, the reaction mixture was decolorized, desalted and concentrated under reduced pressure as in the case of Example 3 to make into a clear syrup comprising L-sorbose. The syrup was purified by subjecting to column chromatography using the slat-form strongly acidic cation-exchange resin as in the case of Example 3, and the resulting L-sorbose fraction was concentrated; and then a syrupy L-sorbose was obtained in a yield of about 25%, on a dry solid basis. The physicochemical properties of the product were identical with those of the standard L-sorbose. The product can be advantageously used as sweetener, carbon source for fermentation, reagent, chemical, material or intermediate for pharmaceuticals, etc. Since the reaction is reversible, L-tagatose can be easily produced by using L-sorbose as the material.

EXAMPLE 7

Immobilized Ketose 3-epimerase

*Rhizobium leguminosarum* ATCC14480 was cultured by the similar method in Example 1, and the resulting culture broth was centrifuged to obtain 100 g of wet-cells having ketose 3-epimerase activity. Successively, the wet-cells were admixed with 100 ml of 2.5% sodium alginate solution which was prepared by dissolving sodium alginate, commercialized by Wako Pure Chemical Industries, Osaka, Japan, into 20 mM Tris-HCl buffer (pH 8.0). The resulting slurry was continuously dropped from a height of about 20 cm from water surface into a 0.1 M calcium chloride solution with stirring by using a magnetic stirrer to make into spherical gel beads with a diameter of about 2 mm. After keeping the beads in the 0.1 M calcium chloride solution for about two hours, the beads were collected by filtrating with aspiration as alginate-immobilized cell beads. Since the immobilized cell beads exhibit ketose 3-epimerase activity, the beads can be advantageously used as immobilized ketose 3-epimerase by packing a column with the beads.

INDUSTRIAL APPLCABILITY

When ketose 3-epimerase of the present invention is allowed to act on free D- or L-ketohexose or D- or L-ketopentose, the enzyme easily produces corresponding D- or L-ketohexose or D- or L-ketopentose by epimerizing the hydroxyl group at the C-3 position of the ketose. The reaction enables us to produce various ketoses, particularly, to produce D-psicose from a material, D-fructose, in a large scale. Therefore, the present invention, establishing the ketose 3-epimerase and its preparation, is a significantly important invention that greatly contribute to the fields of foods, cosmetics, and pharmaceuticals as well as saccharide-manufacturing.

The invention claimed is:

1. An isolated DNA, wherein said DNA is:
   (a) a DNA that encodes a ketose 3-epimerase comprising an amino acid sequence which is at least 90% sequence identical to the amino acid sequence of SEQ ID NO: 2; or
   (b) the full-length complement of a DNA that encodes a ketose 3-epimerase comprising an amino acid sequence which is at least 90% sequence identical to the amino acid sequence of SEQ ID NO: 2.

2. The isolated DNA of claim 1, wherein said DNA comprises:
   (a) the nucleotide sequence of SEQ ID NO: 3, or a nucleotide sequence which is a variant of SEQ ID NO: 3 obtained by deleting, replacing or adding one or more nucleotides to SEQ ID NO: 3.
   (b) the full-length complement of the nucleotide sequence of (a).

3. The isolated DNA of claim 1, which is obtained by replacing one or more nucleotides of SEQ ID NO: 3 without altering the amino acid sequence encoded thereby based on the degeneracy of genetic code.

4. The isolated DNA of claim 1, wherein said DNA consists of the nucleotide sequence of SEQ ID NO: 3, or consists of the full-length complement of the nucleotide sequence of SEQ ID NO: 3.

5. An autonomously replicable vector comprising the isolated DNA of claim 1.

6. A host cell transformed with the autonomously replicable vector of claim 5.

7. A process for producing a recombinant ketose 3-epimerase, comprising the steps of:
   culturing the transformed cell of claim 6; and collecting the formed recombinant ketose 3-epimerase from the resulting culture.

* * * * *